United States Patent
Laura Lapoint et al.

(10) Patent No.: US 9,974,923 B2
(45) Date of Patent: May 22, 2018

(54) SYSTEM AND METHOD FOR PROMPTING A SUBJECT TO ALTER ONE OR MORE BREATHING PARAMETERS

(75) Inventors: Manuel Laura Lapoint, Pittsburgh, PA (US); Sara Marie Sibenaller, Wilkinsburg, PA (US)

(73) Assignee: Koninklijke Philips N.V., Eindhoven (NL)

( * ) Notice: Subject to any disclaimer, the term of this patent is extended or adjusted under 35 U.S.C. 154(b) by 446 days.

(21) Appl. No.: 13/318,017

(22) PCT Filed: Apr. 19, 2010

(86) PCT No.: PCT/IB2010/051709
§ 371 (c)(1),
(2), (4) Date: Oct. 28, 2011

(87) PCT Pub. No.: WO2010/133986
PCT Pub. Date: Nov. 25, 2010

(65) Prior Publication Data
US 2012/0060838 A1   Mar. 15, 2012

Related U.S. Application Data

(60) Provisional application No. 61/179,411, filed on May 19, 2009.

(51) Int. Cl.
*A61M 16/16*   (2006.01)
*A61M 16/00*   (2006.01)
*A61M 16/10*   (2006.01)

(52) U.S. Cl.
CPC ........ *A61M 16/161* (2014.02); *A61M 16/024* (2017.08); *A61M 2016/0027* (2013.01); *A61M 2016/0033* (2013.01); *A61M 2016/102* (2013.01); *A61M 2205/332* (2013.01); *A61M 2205/3368* (2013.01); *A61M 2205/3375* (2013.01); *A61M 2205/3553* (2013.01);
(Continued)

(58) Field of Classification Search
USPC ............ 128/204.18, 204.21–204.23, 205.23, 128/207.14, 207.18
See application file for complete search history.

(56) References Cited

U.S. PATENT DOCUMENTS

| | | |
|---|---|---|
| 4,798,538 A | 1/1989 | Yagi |
| 5,694,939 A | 12/1997 | Cowings |

(Continued)

FOREIGN PATENT DOCUMENTS

| | | |
|---|---|---|
| EP | 2016966 A1 | 1/2009 |
| FR | 2345130 A1 | 10/1977 |

(Continued)

*Primary Examiner* — Rachel T Sippel

(57) ABSTRACT

A subject is prompted to consciously alter one or more breathing parameters of respiration. To prompt the subject to alter one or more breathing parameters, a pressurized flow of breathable gas is provided to the airway of the subject. One or more gas parameters of the gas in the pressurized flow of breathable gas are adjusted to provide breathing cues to the subject that encourage the subject to consciously adjust respiration such that the one or more breathing parameters are altered. Information is also conveyed to the subject through a user interface that dynamically provides information to the subject about the breathing cues.

27 Claims, 3 Drawing Sheets

(52) U.S. Cl.
CPC ............... *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2205/583* (2013.01); *A61M 2230/42* (2013.01); *A61M 2230/43* (2013.01)

(56) References Cited

U.S. PATENT DOCUMENTS

| | | | |
|---|---|---|---|
| 5,906,202 A * | 5/1999 | Schuster et al. | 128/203.23 |
| 6,105,575 A | 8/2000 | Estes et al. | |
| 6,273,088 B1 | 8/2001 | Hillsman | |
| 7,117,032 B2 | 10/2006 | Childre et al. | |
| 2006/0047202 A1* | 3/2006 | Elliott | 600/485 |
| 2007/0017515 A1* | 1/2007 | Wallace et al. | 128/204.23 |
| 2007/0125370 A1* | 6/2007 | Denyer | A61M 15/00 128/200.14 |
| 2008/0017194 A1* | 1/2008 | Hassanein | A01N 1/02 128/200.24 |
| 2008/0035147 A1 | 2/2008 | Kirby et al. | |
| 2008/0319333 A1* | 12/2008 | Gavish et al. | 600/529 |
| 2011/0114607 A1 | 5/2011 | Fiaccabrino et al. | |
| 2012/0003620 A1 | 1/2012 | Pittman et al. | |

FOREIGN PATENT DOCUMENTS

| | | |
|---|---|---|
| JP | 62277976 A | 12/1987 |
| JP | 1043328 A | 2/1998 |
| JP | 2009082175 A | 4/2009 |
| JP | 2012500337 A | 1/2012 |
| JP | 2012520718 A | 9/2012 |
| WO | 2008021222 A2 | 2/2008 |
| WO | 2008110956 A1 | 9/2008 |

* cited by examiner

US 9,974,923 B2

SYSTEM AND METHOD FOR PROMPTING A SUBJECT TO ALTER ONE OR MORE BREATHING PARAMETERS

This patent application claims the priority benefit under 35 U.S.C. § 119(e) of U.S. Provisional Application No. 61/179,411 filed on May 19, 2009, the contents of which are herein incorporated by reference. This application is related to U.S. Patent Application Ser. No. 61/161,881 ("the '881 Application"), entitled "SYSTEM AND METHOD FOR ADJUSTING TIDAL VOLUME OF A SELF-VENTILATING SUBJECT," and filed Mar. 20, 2009. The '881 Application is hereby incorporated into the present application in its entirety.

The invention relates to a system and method for providing breathing cues to a subject that prompt the subject to consciously alter one or more breathing parameters.

It is known that teaching subjects to consciously alter one or more breathing parameters may enhance the health, comfort, and/or performance of the subjects. For example, increasing tidal volume and/or decreasing breath rate has been linked to reducing blood pressure. As another example, subjects may be taught breathing patterns with specific timings, flow rates, pressures, flow rate curve shapes, pressure curve shapes, and/or other parameters for activities like meditation, athletics, aerobic and/or anaerobic activity, yoga, child-birth (e.g., Lamaze breathing), for reception of a positive airway pressure therapy, and/or other activities.

Conventional systems for teaching subjects to consciously alter one or more breathing parameters generate breathing cues that may be difficult for subjects to interpret.

One aspect of the invention relates to a system configured to prompt a subject to consciously alter one or more breathing parameters. In one embodiment, the system comprises a device, a user interface, and a processor. The device is configured to generate a pressurized flow of breathable gas for delivery to the airway of a subject. The user interface is configured to communicate information to the subject related to the operation of the device and/or the pressurized flow of breathable gas. The processor is configured (i) to control the device such that the device adjusts one or more gas parameters of the gas in the pressurized flow of breathable gas in order to provide breathing cues to the subject that prompt the subject to consciously alter one or more breathing parameters of respiration, and (ii) to control the user interface such that the user interface communicates information to the subject related to the meaning of the breathing cues provided to the subject by the pressurized flow of breathable gas generated by the device.

Another aspect of the invention relates to a method of prompting a subject to consciously alter one or more breathing parameters. In one embodiment, the method comprises generating a pressurized flow of breathable gas for delivery to the airway of a subject; adjusting one or more gas parameters of the gas in the pressurized flow of breathable gas in order to provide breathing cues to the subject that prompt the subject to consciously alter one or more breathing parameters of respiration; and communicating information to the subject related to the meaning of the breathing cues provided to the subject by the pressurized flow of breathable gas, wherein the information is communicated to the subject dynamically with the provision of the breathing cues.

Yet another aspect of the invention relates to a system configured to prompt a subject to consciously alter one or more breathing parameters. In one embodiment, the system comprises means for generating a pressurized flow of breathable gas for delivery to the airway of a subject; means for adjusting one or more gas parameters of the gas in the pressurized flow of breathable gas in order to provide breathing cues to the subject that prompt the subject to consciously alter one or more breathing parameters of respiration; and means for communicating information to the subject related to the meaning of the breathing cues provided to the subject by the pressurized flow of breathable gas, wherein the information is communicated to the subject dynamically with the provision of the breathing cues.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
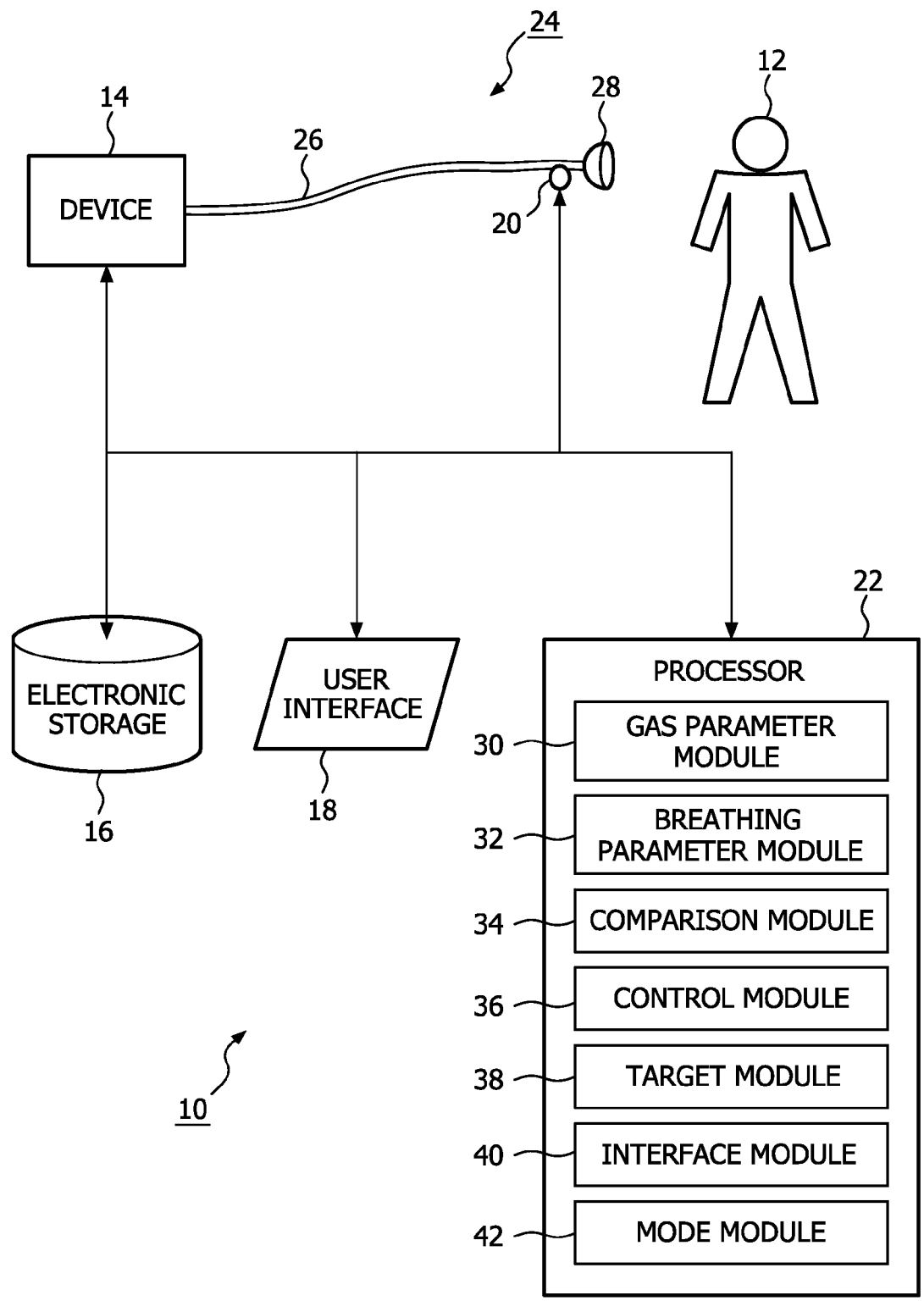
FIG. 1 illustrates a system configured to prompt a subject to consciously alter one or more breathing parameters, in accordance with one or more embodiments of the invention.

FIG. 1 illustrates a system 10 configured to prompt a subject 12 to consciously alter one or more breathing parameters of the respiration of subject 12. To prompt subject 12 to alter one or more breathing parameters, system 10 provides pressurized flow of breathable gas to the airway of subject 12. The system 10 adjusts one or more gas parameters of the gas in the pressurized flow of breathable gas to provide breathing cues to subject 12 that encourage subject 12 to consciously adjust respiration such that the one or more breathing parameters are altered. The breathing cues provided to subject 12 prompt subject 12 to consciously alter the one or more breathing parameters to conform to a breathing regime. The breathing regime may include, for example, a period of increased tidal volume and/or reduced breath rate, a yoga breathing regime, a meditation breathing regime, a breathing regime for use during aerobic and/or anaerobic exercise, a Lamaze breathing regime, a breathing regime for use during a pressure support therapy, and/or other breathing regimes. The system 10 is further configured to provide information to subject 12 related to the breathing cues being delivered (or about to be delivered) by system 10 via the pressurized flow of breathable gas. This information may be provided to the user auditorily, visually, tactily, and/or via some other sensory feedback. The information related to the breathing cues may train subject 12 to understand the breathing cues delivered through the pressurized flow of breathable gas. In one embodiment, system 10 may include a device 14, electronic storage 16, a user interface 18, one or more sensors 20, a processor 22, and/or other components.

In one embodiment, device 14 includes a positive pressure support device. A positive pressure support device is well-known and is disclosed, for example, in U.S. Pat. No. 6,105,575, hereby incorporated by reference in its entirety. In this embodiment, device 14 is configured to deliver a pressurized flow of breathable gas to the airway of subject 12.

Device 14 may be configured to generate the pressurized flow of breathable gas according to one or more modes. A non-limiting example of one such mode is Continuous Positive Airway Pressure (CPAP). CPAP has been used for many years and has proven to be helpful in promoting regular breathing. Another mode for generating the pressurized flow of breathable gas is Inspiratory Positive Air Pressure (IPAP). One example of the IPAP mode is bi-level positive air pressure (BiPAP). In BiPAP, two levels of positive air pressure (HI and LO) are supplied to a patient. Other modes of generating the pressurized flow of breathable gas are contemplated.

Generally, the timing of the HI and LO levels of pressure are controlled such that the HI level of positive air pressure is delivered to subject 12 during inhalation and the LO level of pressure is delivered to subject 12 during exhalation. In conventional positive pressure support devices, the timing of the HI and LO levels of pressure is coordinated to coincide with the breathing of subject 12 based on detection of gas parameters that indicate whether a user is currently inhaling or exhaling.

The pressurized flow of breathable gas is delivered to the airway of subject 12 via a subject interface 24. Subject interface 24 is configured to communicate the pressurized flow of breathable gas generated by device 14 to the airway of subject 12. As such, subject interface 24 includes a conduit 26 and an interface appliance 28. Conduit conveys the pressurized flow of breathable gas to interface appliance 28, and interface appliance 28 delivers the pressurized flow of breathable gas to the airway of subject 12. Some examples of interface appliance 28 may include, for example, an endotracheal tube, a nasal cannula, a tracheotomy tube, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

In one embodiment, electronic storage 16 comprises electronic storage media that electronically stores information. The electronically storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., device 14, user interface 18, processor 22, etc.).

User interface 18 is configured to provide an interface between system 10 and subject 12 through which subject 12 may provide information to and receive information from system 10. This enables data, results, and/or instructions and any other communicable items, collectively referred to as "information," to be communicated between the subject 12 and one or more of device 14, electronic storage 16, and/or processor 22. Examples of interface devices suitable for inclusion in user interface 18 include a keypad, buttons, switches, a keyboard, knobs, levers, a display screen, a touch screen, speakers, a microphone, an indicator light, an audible alarm, a printer, and/or other interface devices. In one embodiment, user interface 18 includes a plurality of separate interfaces. In one embodiment, user interface 18 includes at least one interface that is provided integrally with device 14.

It is to be understood that other communication techniques, either hard-wired or wireless, are also contemplated by the present invention as user interface 18. For example, the present invention contemplates that user interface 2180 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

One or more sensors 20 are configured to generate one or more output signals conveying information related to one or more gas parameters of the gas breathed by subject 12. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. In an embodiment in which a pressurized flow of breathable gas is delivered to subject 12 from device 14, sensors 20 include sensors in communication with gas within subject interface 24.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device, or processor 22 may represent processing functionality of a plurality of devices operating in coordination.

As is shown in FIG. 1, processor 22 may be configured to execute one or more computer program modules. The one or more computer program modules may include one or more of a gas parameter module 30, a breathing parameter module 32, a comparison module 34, a control module 36, a target module 38, an interface module 40, a mode module 42, and/or other modules. Processor 22 may be configured to execute modules 30, 32, 34, 36, 38, 40, and/or 42 by software; hardware; firmware; some combination of software, hardware, and/or firmware; and/or other mechanisms for configuring processing capabilities on processor 22.

It should be appreciated that although modules 30, 32, 34, 36, 38, 40, and 42 are illustrated in FIG. 1 as being co-located within a single processing unit, in implementations in which processor 22 includes multiple processing units, one or more of modules 30, 32, 34, 36, 38, 40, and/or 42 may be located remotely from the other modules. The description of the functionality provided by the different modules 30, 32, 34, 36, 38, 40, and/or 42 described below is for illustrative purposes, and is not intended to be limiting, as any of modules 30, 32, 34, 36, 38, 40, and/or 42 may provide more or less functionality than is described. For example, one or more of modules 30, 32, 34, 36, 38, 40, and/or 42 may be eliminated, and some or all of its functionality may be provided by other ones of modules 30, 32, 34, 36, 38, 40, and/or 42. As another example, processor 22 may be configured to execute one or more additional modules that may perform some or all of the functionality attributed below to one of modules 30, 32, 34, 36, 38, 40, and/or 42.

The gas parameter module 30 is configured to determine information related to one or more gas parameters of the pressurized flow of breathable gas that is generated by device 14 and delivered to the airway of subject 12 via subject interface 24. The one or more gas parameters are determined based on the output signals of sensors 20. The one or more gas parameters may include one or more of a pressure, a flow rate, a peak flow, a composition, a humidity, a temperature, an acceleration, a velocity, a thermal energy dissipated (e.g., in a mass flowmeter, etc.), and/or other gas parameters.

The breathing parameter module 32 is configured to determine one or more breathing parameters of the respiration of subject 12. The breathing parameter module 32 may determine the one or more breathing parameters based on the one or more gas parameters determined by gas parameter module 30 and/or from the output signals generated by sensors 20. The one or more breathing parameters include the one or more breathing parameters that subject 12 is prompted to consciously alter by the breathing cues provided in the pressurized flow of breathable gas. For example, the one or more breathing parameters may include one or more of an inhalation flow rate, an inhalation period, an exhalation flow rate, an exhalation period, a tidal volume, a breathing rate, a breath period, a peak flow, a flow curve shape, a pressure curve shape, and/or other breathing parameters.

Comparison module 34 is configured to compare the one or more breathing parameters determined by breathing parameter module 32 to a target for the one or more breathing parameters that the breathing cues prompt subject 12 to consciously alter. For example, if the breathing parameter is tidal volume, the target is a target tidal volume. As another example, if the breathing parameter is a curve shape (e.g., of a pressure or flow curve of respiration), the target may include a target curve shape. Other examples of appropriate targets (e.g., for the breathing parameters enumerated above) will be apparent.

Control module 36 is configured to control device 14. Controlling device 14 includes adjusting the breathing cues provided to subject 12 by device 14. As was mentioned above, in one embodiment, the breathing cues administered to subject 12 by device 14 include changes to one or more parameters of the pressurized flow of breathable gas delivered from device 14 to subject 12. For example, the one or more parameters may include a pressure, a flow rate, and/or a volume of the pressurized flow of breathable gas. Control module 36 adjusts the breathing cues provided to subject 12 be device 14 in order to prompt subject 12 to bring the one or more breathing parameters into conformance with the target.

For example, in an embodiment in which device 14 generates the pressurized flow of breathable gas according to a BiPAP mode, control module 36 may control device 14 to adjust the pressure, flow rate, and/or volume of gas delivered to the airway of subject 12 while the pressurized flow of breathable gas is being generated at the HI pressure (e.g., during inhalation). Adjusting the pressure, flow rate, and/or volume of gas delivered to the airway of subject 12 while the pressurized flow of breathable gas is being generated at the HI pressure will tend to generate breathing cues that prompt subject 12 to alter the volume of gas inhaled, to alter the inspiration period, to alter the inspiration flow rate, to alter the tidal volume, and/or to otherwise consciously alter one or more other breathing parameters.

As another example, in an embodiment in which device 14 generates the pressurized flow of breathable gas according to a BiPAP mode, control module 36 may control device 14 to adjust the pressure flow rate, and/or volume of gas delivered to the airway of subject 12 while the pressurized flow of breathable gas is being generated at the LO pressure (e.g., during exhalation). Adjusting the pressure, flow rate, and/or volume of gas delivered to the airway of subject 12 while the pressurized flow of breathable gas is being generated at the LO pressure may result in breathing cues that tend to prompt subject 12 to adjust the exhalation period, the exhalation flow rate, the peak flow of respiration, the tidal volume, and/or to otherwise consciously alter one or more other breathing parameters.

As yet another example, in an embodiment in which device 14 generates the pressurized flow of breathable gas according to a BiPAP mode, control module 36 may control device 14 to adjust a period of the HI and/or LO pressure cycles, a pressure curve shape during a transition between HI and LO pressure cycles, a flow rate curve shape during a transition between HI and LO pressure cycles, and/or adjust other gas parameters of the pressurized flow of breathable gas. As will be appreciated, such adjustments to the gas parameters of the pressurized flow of breathable gas will tend to provide breathing cues to subject 12 to consciously alter one or more breathing parameters. For example, such breathing cues may prompt subject 12 to alter one or more of a breathing rate, a breath period, a respiration flow curve shape, a respiration pressure curve shape, and/or other breathing parameters.

In one embodiment, adjustments to the parameters of the pressurized flow of breathable gas are made by control module 36 in a feedback manner. In this embodiment, adjustments to the parameters of the pressurized flow of breathable gas may be determined based on the comparison between the breathing parameter and the target threshold made by comparison module 34. For example, if comparison module 34 determines that the gas parameters of the pressurized flow of breathable gas that are being adjusted to provide breathing cues to subject 12 are not adequate, control module 36 will adjust the gas parameters of the pressurized flow of breathable gas to provide more effective cues. Breathing cues would be identified as inadequate if comparison module 34 determines that the breathing cues are not successful in prompting subject 12 to consciously bring the one or more breathing parameters into conformance with the target for the one or more breathing parameters. This adjustment may include adjustments for instances in which the conscious alteration of the one or more breathing parameters by subject 12 has not gone far enough (e.g., breathing is too close to normal breathing), and/or for instances in which the conscious alteration of the one or more breathing parameters by subject 12 has gone too far.

In one embodiment, adjustments to the parameters of the pressurized flow of breathable gas are not made in a feedback manner. In this embodiment, relationships between the one or more gas parameters of the pressurized flow of breathable gas and the one or more breathing parameters to be consciously altered are determined in advance. These predetermined relationships are then used to generate the pressurized flow of breathable gas with gas parameters that correspond to the target for the one or more breathing parameters. In this embodiment, processor 22 may not include comparison module 34 and/or sensors 20.

Target module 38 is configured to obtain a target for the one or more breathing parameters to be consciously altered. In one embodiment, the target is received from a user (e.g., a caregiver, subject 12, etc.). The user may input the target via user interface 18. Inputting the target may include inputting a new target, or adjusting a previously obtained target. Inputting the target may include configuring the target from a predetermined template (e.g., corresponding to a certain breathing regime).

In one embodiment, the target is determined by target module 38 based on a determination of the typical levels of the one or more breathing parameters of subject 12. For example, the target may be set at a predetermined amount above the levels for the one or more breathing parameters of subject 12. A determination of the typical one or more breathing parameters of subject 12 may be based on determinations by breathing parameter module 32, information stored in electronic storage 16 for subject 12, and/or other sources.

The target for the one or more breathing parameters corresponds to a breathing regime. For example, a breathing regime including a period of increased tidal volume and/or reduced breath rate, the target may include a target level for tidal volume, breath rate, and/or one or more related breathing parameters. As another example, for a breathing regime associated with a specific pressure and/or flow rate curve shape (e.g., a yoga breathing regime, a meditation breathing regime, a breathing regime for use during aerobic and/or anaerobic exercise, a Lamaze breathing regime, etc.), the target may include a target curve shape. The target curve shape may be refined (e.g., by a user via user interface 18) to a target curve having values for the extrema (e.g., maxima and/or minima). Other targets corresponding to these and/or other breathing regimes may be implemented within the scope of this disclosure.

In one embodiment, target module 38 sets the target at an initial target, and then slowly modifies the target over time toward a final target. The initial target may be based on the baseline breathing parameters of subject 12, and/or may be preset (or preconfigured). Modifying the target over time from an initial target to a final target may enhance the comfort of the breathing cues provided to subject 12. Modifying the target over time may include incrementing the target, modifying the target over time smoothly, and/or otherwise modifying the target.

In one embodiment, target module 38 adjusts the target based on the one or more breathing parameters determined by breathing parameter module 32. For example, comparison module 34 may determine that subject 12 is not altering the one or more breathing parameters adequately to conform to the target. Based on this determination, target module 38 may adjust the target to make conformance easier, the breathing cues provided to subject 12 by device 14 may be adjusted by control module 36 to reflect the adjusted target. Target module 38 may then monitor the compliance of subject 12 with the new target (e.g., based on comparisons made by comparison module 34). If it is determined that subject 12 is complying with the new target, target module 38 will then adjust the target toward the previous target. If it is determined that subject 12 is not complying with the new target, then target module 38 will take a different action. For instance, target module 36 may maintain the target tidal volume at a constant level until subject 12 begins to comply, or target module 38 may adjust the target to reduce the required to comply with the target until subject 12 is again in compliance before resuming the modification of the target toward a final target.

The breathing cues provided to subject 12 by manipulating one or more gas parameters of the pressurized flow of breathable gas may be an effective way to provide respiratory instruction to subject 12 to consciously alter one more breathing parameters. The conscious alteration of the one or more breathing parameters in response to the breathing cues may enable subject 12 to receive therapeutic benefits during the altered breathing, or to learn to consciously modify the one or more breathing parameters during periods when subject 12 is not connected to device 14. For example, subject 12 may learn to breathing regimes appropriate to and/or effective for specific activities (e.g., sports, athletic training, yoga, meditation, etc.) that can be executed (once learned) without the aid of system 10.

However, in some cases, subject 12 may initially have difficulty determining what the breathing cues being provided in the pressurized flow of breathable gas are prompting subject 12 to do. The interface module 40 is configured to dynamically (e.g., adjusted or updated based on the actual breathing cues) to provide information to subject 12 related to the meaning of the breathing cues provided to the subject by the pressurized flow of breathable gas generated by device 14. In one embodiment, interface module 40 controls user interface 18 to communicate the information related to the breathing cues to subject 12. The information related to the breathing cues may include, for example, instructions to begin exhaling, to end exhaling, to begin inhaling, to end inhaling, to breathe faster, to breathe slower, to increase flow, to decrease flow, to pause respiration, and/or to otherwise consciously alter one or more breathing parameters.

The information related to the breathing cues may be provided to subject 12 by user interface 18 in the form of auditory signals, visual signals, tactile signals, and/or other sensory signals. By way of non-limiting example, user interface 18 may include a radiation source capable of emitting light. The radiation source may include, for example, one or more of at least one LED, at least one light bulb, a display screen, and/or other sources. The interface module 40 may control the radiation source to emit light in a manner that conveys to subject 12 information related to the breathing cues being provided to subject 12 by the pressurized flow of breathable gas. For instance, the radiation source may emit light when the breathing cues are prompting subject 12 to inhale, and may stop emitting light, or emit light of a different color, when the breathing cues are prompting subject 12 to exhale. The intensity of the light emitted by the radiation source may convey to subject 12 the magnitude of the flow that the breathing cues are prompting subject 12 to generate during respiration.

Figure 2:
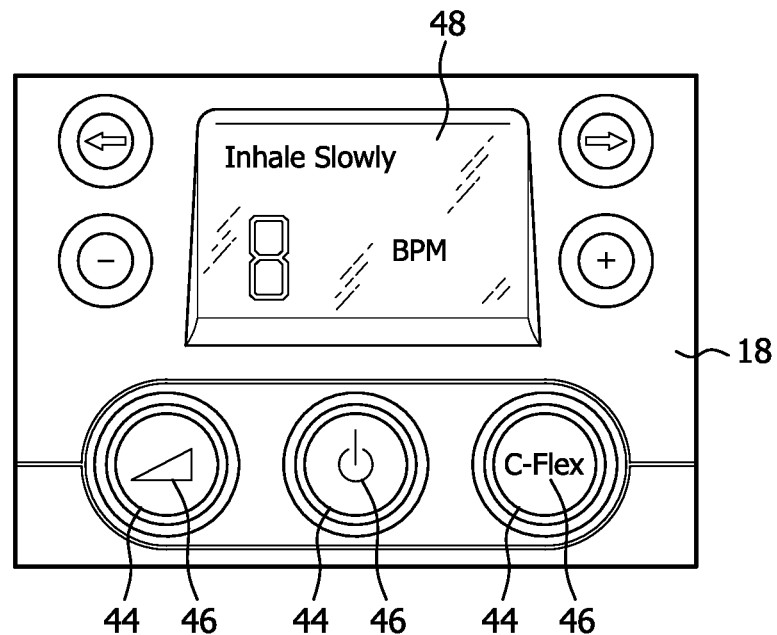
FIG. 2 illustrates a user interface configured to provide information to a subject related to breathing cues being provided to the subject, according to one or more embodiments of the invention.
Figure 3:
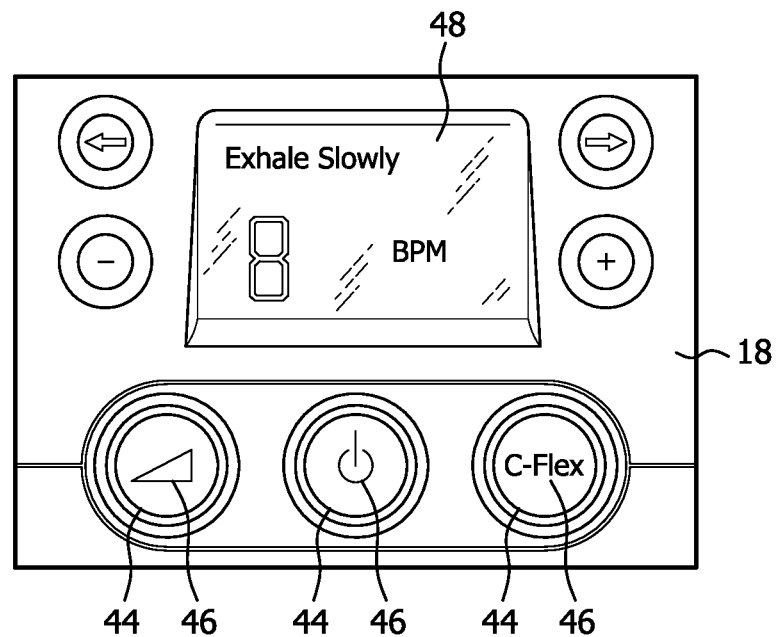
FIG. 3 illustrates a user interface configured to provide information to a subject related to breathing cues being provided to the subject, according to one or more embodiments of the invention.

FIGS. 2 and 3 illustrate an embodiment in which interface module 40 controls a plurality of radiation sources 44 included in user interface 18 to emit radiation in a manner that provides information about the breathing cues being delivered by the pressurized flow of breathable gas. In particular, the plurality of radiation sources 44 are integrated with a set of buttons 46 disposed on device 14 to control device 14. In the embodiment illustrated in FIGS. 2 and 3, radiation sources 44 emit radiation when the breathing cues are prompting subject 12 to inhale, and stop emitting radiation when the breathing cues are prompting subject 12 to exhale.

Returning to FIG. 1, as another non-limiting example of the manner in which user interface 18 may communicate information about the breathing cues to subject 12, user interface 18 may include one or more elements capable of generating sounds that are audible to subject 12. The interface module 40 may control the element(s) to generate sounds that communicate to subject 12 the meaning of the cues being delivered to subject 12 by the pressurized flow of breathable gas. For instance, interface module 40 may control the element(s) to emit a "beep" or other short burst of noise to indicate to subject 12 a transition between inhalation and exhalation, and/or that flow should be increased or decreased. The interface module 40 may control the element(s) to play word messages that indicate to subject 12 the meaning of the breathing cues. The word messages may be prerecorded and stored within electronic storage 16.

As another non-limiting example of the manner in which user interface 18 may communicate information about the breathing cues to subject 12, user interface 18 may include one or more devices that contact subject 12 and provide tactile feedback to subject 12. For instance, user interface 18 may include a cuff that is worn by subject 12 around an extremity such as an arm, a leg, a finger, and/or other extremities. The cuff may carry one or more sensors configured to detect a physiological parameter of subject 12, such as for example, pulse, pulse rate, respiratory effort, blood pressure, blood oxygenation, and/or other physiological parameters. The cuff may vibrate and/or tighten on the extremity of subject 12 to provide information about the breathing cues to subject 12, such as a transition between inhalation and/or exhalation, or that flow should be increased or decreased.

As another non-limiting example of the manner in which user interface 18 may communicate information about the breathing cues to subject 12, user interface 18 may include a display screen that provides subject 12 with text conveying information about the breathing cues. The display screen may include, for instance, a screen provided on device 14 and/or other display screens. For instance, FIGS. 2 and 3 illustration user interface 18 including a display screen 48 for conveying information to subject 12 about the breathing cues being delivered by the pressurized flow of breathable gas.

Figure 4:
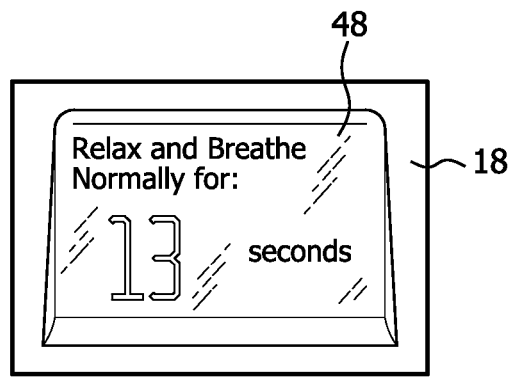
FIG. 4 illustrates a user interface configured to provide information to a subject related to breathing cues being provided to the subject, according to one or more embodiments of the invention.
Figure 5:
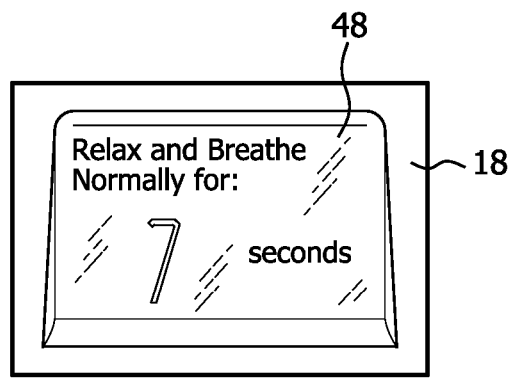
FIG. 5 illustrates a user interface configured to provide information to a subject related to breathing cues being provided to the subject, according to one or more embodiments of the invention.
Figure 6:
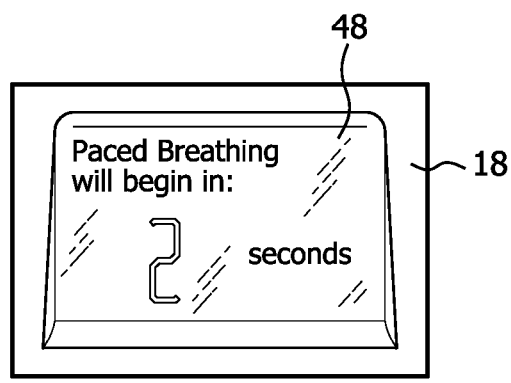
FIG. 6 illustrates a user interface configured to provide information to a subject related to breathing cues being provided to the subject, according to one or more embodiments of the invention.

In one embodiment, interface module 40 controls user interface 18 to provide information about breathing cues that are currently being delivered to subject 12 and/or future breathing cues. By way of example, FIGS. 4-6 illustrate an embodiment of user interface 18 including display screen 48 in which interface module 40 controls display screen 48 to provide information to subject 12 regarding upcoming breathing cues.

Referring back to FIG. 1, mode module 42 is configured to manage the mode in which system 10 is operating. The modes in which system 10 is capable of operating may include modes corresponding to individual breathing regimes. A mode that corresponds to a breathing regime will enable target module 38 to obtain a target that will result in the generation of breathing cues prompting subject 12 to breath in accordance with the breathing regime. For example, mode/setting module 42 may enable system 10 to operate according to modes corresponding to one or more of a period of increased tidal volume and/or reduced breath rate, a yoga breathing regime, a meditation breathing regime, a breathing regime for use during aerobic and/or anaerobic exercise, a Lamaze breathing regime, a breathing regime for use during a pressure support therapy, and/or other breathing regimes. Another mode, or set of modes, managed by mode/setting module 42 may include learning modes in which interface module 40 controls user interface 18 to communicate information to subject 12 about the breathing cues being delivered through the pressurized flow of breathable gas, and normal modes in which information about the breathing cues is not provided to subject 12 through user interface 18.

The mode module 42 may be configured to enable subject 12 to manually switch between a learning mode and a normal mode. This would enable subject 12 to selectively disable the provision of information to subject 12 through user interface 18 about the breathing cues. Similarly, mode module 42 may be configured to enable subject 12 to manually select a mode corresponding to a particular breathing regime (e.g., a learning mode and/or a normal mode corresponding to the breathing regime). Inputs to mode module 42 to select a mode of operation for system 10 may be accomplished by subject 12 (or some other user) via user interface 18.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system figured to prompt a subject to consciously alter one or more breathing parameters, the system comprising:
   a positive pressure support device configured to generate a pressurized flow of breathable gas for delivery to the airway of a subject, wherein the pressurized flow of breathable gas comprises one or more gas parameters, wherein the positive pressure support device is further configured to provide breathing cues and adjusted breathing cues to the subject by adjustments of the one or more gas parameters of the pressurized flow of breathable gas, and wherein the breathing cues and the adjusted breathing cues prompt the subject to consciously make an adjustment to one or more breathing parameters of respiration of the subject; and a processor configured to:
(i) control the positive pressure support device to generate the pressurized flow of breathable gas according to a predetermined pressure therapy regime;
(ii) determine one or more targets for the one or more breathing parameters according to the predetermined pressure therapy regime;
(iii) control the positive pressure support device such that the positive pressure support device provides the breathing cues and the adjusted breathing cues;
(iv) determine whether the one or more breathing parameters satisfy the one or more targets;
(v) responsive to the one or more breathing parameters not satisfying the one or more targets, adjust the breathing cues such that the conscious adjustment by the subject causes the one or more breathing parameters to satisfy an adjusted target, wherein each of the one or more targets and the adjusted target includes a different target curve shape; and
(vii) responsive to the breathing cues being adjusted and the one or more breathing parameters satisfying the adjusted target, readjust the breathing cues such that the conscious adjustment by the subject causes the one or more breathing parameters to satisfy the one or more targets.

2. The system of claim 1, further comprising:
a user interface configured to communicate information to the subject related to the operation of the device and/or the pressurized flow of breathable gas,
wherein the user interface includes a display screen configured to provide text conveying the information,
wherein the processor is further configured to control the user interface such that the user interface provides text through the display screen,
wherein the text communicates information to the subject related to the meaning of the breathing cues provided to the subject, and
wherein the information related to the meaning of the breathing cues communicated by the user interface to the subject comprises an indication of whether a current breathing cue is prompting the subject to inhale or exhale.

3. The system of claim 2, wherein the text provided through the display screen communicates information related to the meaning of the breathing cues that will be provided to the subject such that the text provided through the display screen corresponds to an upcoming breathing cue that has yet to be provided to the subject, wherein the information communicated by the display screen includes a countdown to the upcoming breathing cue.

4. The system of claim 2, wherein the one or more gas parameters of the pressurized flow of breathable gas that are adjusted to provide the breathing cues to the subject comprise one or both of pressure and/or flow rate, wherein the user interface further includes one or more elements capable of generating sounds that are audible to the subject, and wherein the processor is further configured to control the user interface such that the one or more elements capable of generating sounds play word messages that indicate the meaning of the breathing cues provided to the subject.

5. The system of claim 2, wherein the processor is further configured to facilitate selective disabling by the subject of the provision of information related to the breathing cues.

6. The system of claim 2, wherein a user manually switches from a learning mode to a normal mode to selectively disable the provision of the meaningful text to the user through the user interface.

7. The system of claim 1, wherein the one or more breathing parameters that the breathing cues prompt the subject to consciously make the adjustment comprise one or more of an inhalation flow rate, an inhalation period, an exhalation flow rate, an exhalation period, a tidal volume, a breathing rate, a breath period, a peak flow, a flow curve shape, or a pressure curve shape.

8. The system of claim 1, wherein the predetermined pressure therapy regime is a period of increased tidal volume and/or reduced breath rate, a yoga breathing regime, a meditation breathing regime, a breathing regime for use during aerobic and/or anaerobic exercise, a Lamaze breathing regime, or a breathing regime for use during a pressure support therapy.

9. The system of claim 1, wherein determining the one or more targets comprises incrementally increasing levels of the one or more breathing parameters, wherein incrementally increasing levels of the one or more breathing parameters start at one or more initial targets and incrementally increase to one or more final targets.

10. The system of claim 1, wherein one or more of the target curve shapes are refined by a user via the user interface.

11. The system of claim 10, wherein each of the one or more target curve shapes is refined by at least adjusting values of the curve's extrema.

12. The system of claim 1, wherein the processor is further configured to: (vii) responsive to the one or more breathing parameters not satisfying the adjusted target, readjust the breathing cues such that the conscious adjustment by the subject causes the one or more breathing parameters to satisfy a further adjusted version of the one or more targets, wherein the further adjusted version of the one or more targets includes a different target curve shape.

13. The system of claim 1, wherein the not satisfying of the one or more targets comprises exceeding the one or more targets too far.

14. A method of prompting a subject to consciously alter one or more breathing parameters, the method comprising:
generating, via a positive pressure support device, a pressurized flow of breathable gas for delivery to the airway of a subject, wherein the pressurized flow of breathable gas comprises one or more gas parameters;
controlling the pressurized flow of breathable gas according to a predetermined pressure therapy regime;
providing, via the pressurized flow of breathable gas of the positive pressure support device, breathing cues and adjusted breathing cues to the subject, wherein the breathing cues and the adjusted breathing cues prompt the subject to consciously make an adjustment to one or more breathing parameters of respiration of the subject;
determining one or more targets for the one or more breathing parameters according to the predetermined pressure therapy regime;
determining whether the one or more breathing parameters satisfy the one or more targets;

responsive to the one or more breathing parameters not satisfying the one or more targets, adjusting the breathing cues such that the conscious adjustment by the subject causes the one or more breathing parameters to satisfy an adjusted target, wherein each of the one or more targets and the adjusted target includes a different target curve shape; and responsive to the breathing cues being adjusted and the one or more breathing parameters satisfying the adjusted target, readjusting the breathing cues such that the conscious adjustment by the subject causes the one or more breathing parameters to satisfy the one or more targets.

15. The method of claim 14, further comprising:
communicating information, by a user interface that includes a display screen configured to provide text conveying the information, to the subject,
wherein the text communicates information to the subject related to the meaning of the breathing cues provided to the subject,
wherein the information related to the meaning of the breathing cues communicated to the subject comprises an indication of whether a current breathing cue is prompting the subject to inhale or exhale.

16. The method of claim 15, wherein the text provided through the display screen communicates information related to the meaning of the breathing cues that will be provided to the subject such that the text provided through the display screen corresponds to an upcoming breathing cue that has yet to be provided to the subject, wherein the information provided by the display screen includes a countdown to the upcoming breathing cue.

17. The method of claim 15, wherein the one or more gas parameters of the pressurized flow of breathable gas that are adjusted to provide the breathing cues to the subject comprise one or both of pressure and/or flow rate, wherein the user interface further includes one or more elements capable of generating sounds that are audible to the subject, the method further comprising:
controlling the user interface such that the one or more elements capable of generating sounds play word messages that indicate the meaning of the breathing cues provided to the subject.

18. The method of claim 14, wherein the one or more breathing parameters that the breathing cues prompt the subject to consciously make the adjustment comprise one or more of an inhalation flow rate, an inhalation period, an exhalation flow rate, an exhalation period, a tidal volume, a breathing rate, a breath period, or a peak flow.

19. The method of claim 14, wherein the predetermined pressure therapy regime is a period of increased tidal volume and/or reduced breath rate, a yoga breathing regime, a meditation breathing regime, a breathing regime for use during aerobic and/or anaerobic exercise, a Lamaze breathing regime, or a breathing regime for use during a pressure support therapy.

20. The method of claim 14, wherein determining the one or more targets comprises incrementally increasing levels of the one or more breathing parameters, wherein incrementally increasing levels of the one or more breathing parameters start at one or more initial targets and incrementally increase to one or more final targets.

21. A system configured to prompt a subject to consciously alter one or more breathing parameters, the system comprising:

means for generating a pressurized flow of breathable gas for delivery to the airway of a subject, wherein the pressurized flow of breathable gas comprises one or more gas parameters;

means for controlling the pressurized flow of breathable gas according to a predetermined pressure therapy regime;

means for providing breathing cues and adjusted breathing cues to the subject, wherein the breathing cues and the adjusted breathing cues prompt the subject to consciously make an adjustment to one or more breathing parameters of respiration of the subject;

means for determining one or more targets for the one or more breathing parameters according to the predetermined pressure therapy regime;

means for determining whether the one or more breathing parameters satisfy the one or more targets;

means for adjusting, responsive to the one or more breathing parameters not satisfying the one or more targets, the breathing cues such that the conscious adjustment by the subject causes the one or more breathing parameters to satisfy an adjusted target, wherein each of the one or more targets and the adjusted target includes a different target curve shape; and means for readjusting, responsive to the breathing cues being adjusted and the one or more breathing parameters satisfying the adjusted target, the breathing cues such that the conscious adjustment by the subject causes the one or more breathing parameters to satisfy the one or more targets.

22. The system of claim 21, further comprising:
means for communicating information, wherein the means for communication includes a display screen configured to provide text conveying the information, to the subject,
wherein the text communicates information to the subject related to the meaning of the breathing cues provided to the subject,
wherein the information related to the meaning of the breathing cues communicated to the subject comprises an indication of whether a current breathing cue is prompting the subject to inhale or exhale.

23. The system of claim 22, wherein the text provided through the display screen communicates information related to the meaning of the breathing cues that will be provided to the subject such that the text provided through the display screen corresponds to an upcoming breathing cue that has yet to be provided to the subject, wherein the information communicated by the display screen includes a countdown to the upcoming breathing cue.

24. The system of claim 22, wherein the one or more gas parameters of the pressurized flow of breathable gas that are adjusted to provide the breathing cues to the subject comprise one or both of pressure and/or flow rate, wherein the means for communicating information further includes one or more elements capable of generating sounds that are audible to the subject, wherein the means for communicating information is further configured to play word messages that indicate the meaning of the breathing cues provided to the subject.

25. The system of claim 21, wherein the one or more breathing parameters that the breathing cues prompt the subject to consciously make the adjustment comprise one or more of an inhalation flow rate, an inhalation period, an exhalation flow rate, an exhalation period, a tidal volume, a breathing rate, a breath period, or a peak flow.

26. The system of claim 21, wherein the predetermined pressure therapy regime is a period of increased tidal volume and/or reduced breath rate, a yoga breathing regime, a meditation breathing regime, a breathing regime for use during aerobic and/or anaerobic exercise, a Lamaze breathing regime, or a breathing regime for use during a pressure support therapy.

27. The system of claim 21, wherein determining the one or more targets comprises incrementally increasing levels of the one or more breathing parameters, wherein incrementally increasing levels of the one or more breathing parameters start at one or more initial targets and incrementally increase to one or more final targets.

* * * * *